United States Patent [19]
Wilson

[11] 3,968,711
[45] July 13, 1976

[54] PATTERN CUTTING APPARATUS
[75] Inventor: William Donald Wilson, Barrington, R.I.
[73] Assignee: Huestic Machine Corporation, Bristol, R.I.
[22] Filed: Nov. 24, 1975
[21] Appl. No.: 634,476

[52] U.S. Cl. ........................................ 83/171; 83/565
[51] Int. Cl.² ................................................ B26D 7/10
[58] Field of Search ............................... 83/171, 565

[56] References Cited
UNITED STATES PATENTS
3,017,487   1/1962   Priestly ............................... 83/171
3,540,336   11/1970   Kelsey ............................ 83/565 X Primary Examiner—Willie G. Abercrombie
Attorney, Agent, or Firm—Salter & Michaelson

[57] ABSTRACT

This invention relates to apparatus for cutting patterns from blocks which thereafter may be used as molds for forming radiotherapy shields. The device comprises rigid rod means connected at one end thereof to a frame for pivotal movement therewith and having tracing means at the other end thereof so that a pattern such as the X-ray of a portion of a patient's body may be traced thereby. The pattern traced is transmitted to the intermediate portions of the rigid rod means which includes an offset portion within which a block of plastic material, such as polystyrene foam, is placed. This offset portion is spanned by a spring-loaded, electrically heated wire which serves to cut an opening in the plastic block corresponding to the pattern traced by tracing means. Thereafter the block with the patterned opening cut therefrom is used as a mold for receiving metal shielding material. The metal block so formed is then used as a shielding block to prevent X-rays and the like from contacting that part of the body that has been traced, during subsequent radiotherapy treatment.

10 Claims, 8 Drawing Figures

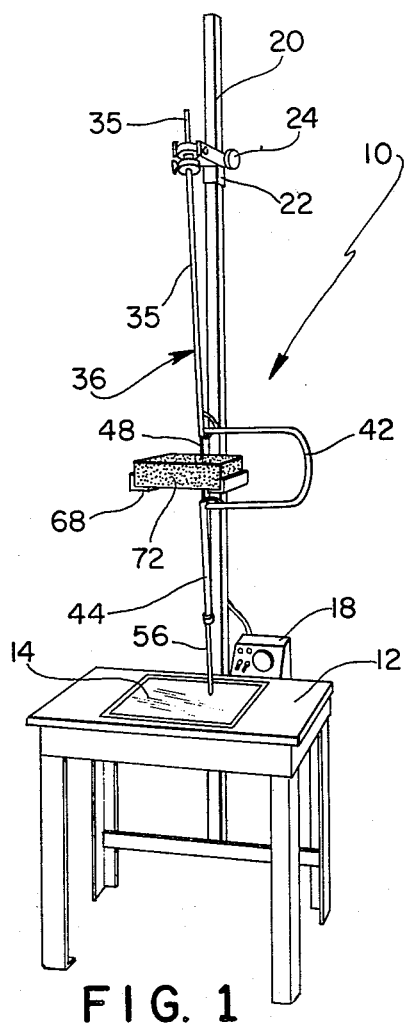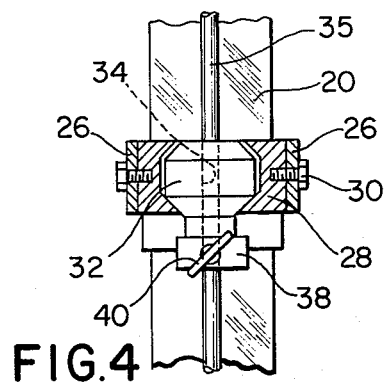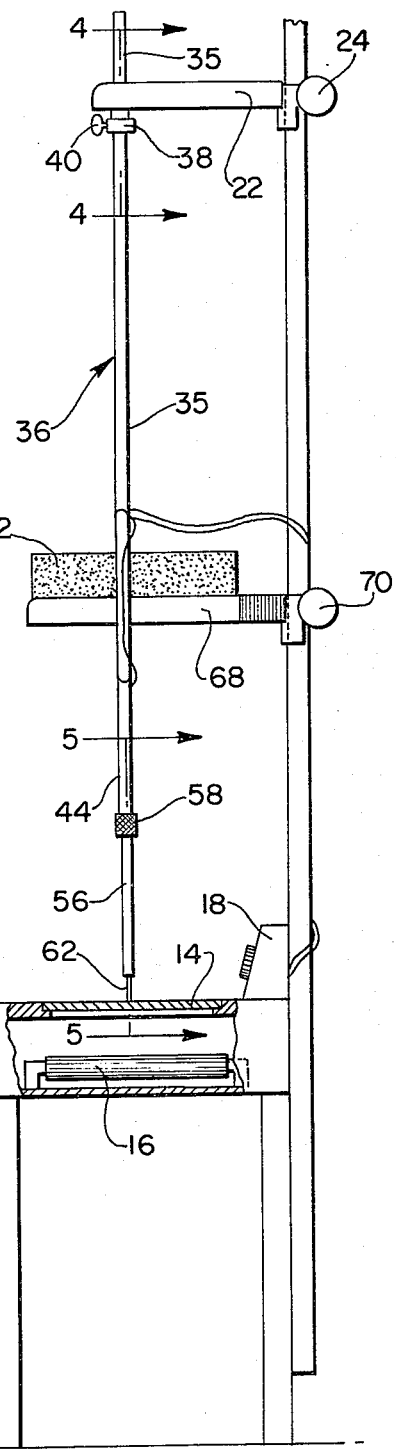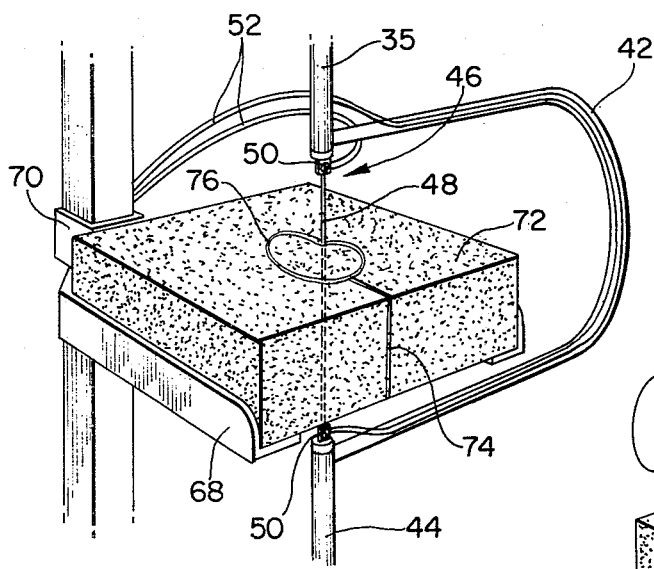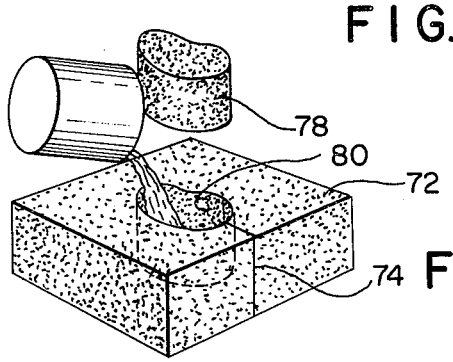

PATTERN CUTTING APPARATUS

BACKGROUND OF THE INVENTION

It is important in radiotherapy treatment of patients to be able to shield portions of the body, such as vital organs, from the effect of such treatment, i.e. in the X-ray treatment of lung diseases it is important to shield the heart from such X-rays. In the past this has been accomplished by the use of metal shielding blocks generally formed from a mold made from foam, resinous material, such as polystyrene block, which is provided with a cutout in a pattern corresponding to that of the area of the particular patient which is to be shielded. Thereafter, the patterned opening in the foam block is filled with shielding material such as lead or special purpose alloys thereof. The thus formed composite foam and shield material block is thereafter used as shield means placed between the treatment source and the patient so as to shield the patterned areas from receiving the treatment rays. Such radiotherapy shielding blocks are presently formed by an apparatus including a lighted table on which an X-ray of the particular person to be treated is placed. Above the table is a platform for retaining a styrofoam block. A frame is provided from which an electrically heated wire is suspended and heavily counterweighted in order to maintain the wire taut. The other end of the wire has a pointer for manually tracing the X-ray exhibited on the lighted table. As the pointer is manipulated to trace the particular section or sections of the X-ray which are to be shielded from the treatment rays, the heated wire automatically cuts a corresponding pattern from the styrofoam block which is mounted above the pointer and within the path of the wire.

With such device, it is important and necessary that the wire be maintained taut by the counterweight in order to insure that a true pattern will be cut from the block. The operation must thus continually work against the counterweight, it being understood that the wire passes over pulleys mounted on the frame whereby the wire may extend as the outline of the X-ray is traced. It is, however, somewhat difficult and fatiguing for an operator to continually operate against such tension during the tracing process, particularly when relatively fine areas are being traced. Furthermore, there is always the possibility that the flexible wire will not cut a true pattern, even though heavily counterweighted. Accordingly, it is desirable to eliminate such operator fatigue while at the same time providing more positive means for maintaining the cutting wire taut to better assure accurate tracing and transmission of the tracing to the block being cut.

SUMMARY OF THE INVENTION

The present invention accomplishes the above-indicated aims, while avoiding the shortcomings of the prior art devices through the provision of apparatus for cutting patterns in mold blocks and the like comprising a frame having a rigid rod pivotally attached thereto at one end thereof. The other end of the rod is provided with tracing means. Intermediate the ends of the rigid rod is a discontinuity, thereby forming upper and lower rod portions connected together by an outwardly offset portion, preferably of C-shaped configuration, having at its open end a heated wire cutting element stretched taut thereacross in substantial alignment with the rigid rod portions. The block to be cut in the desired pattern is mounted within said discontinuity, whereby tracing movement of the rigid rod causes the taut wire to accurately cut the traced pattern in the block. Since the heated wire is tightly held by the rigid rod, no counterweights of any kind are necessary, thus resulting in easier and more accurate cutting of the desired pattern.

Another important feature is the fact that the wire has a spring-loaded mounting, whereby any tendency of the wire to expand and become slack because of the heat present, will automatically be compensated for.

It is therefore a primary object of the instant invention to provide apparatus for cutting patterns in mold blocks that avoids operator fatigue yet simultaneously maintains a taut cutting element so as to accurately reflect the pattern traced.

Another object of the invention is the provision of a device for cutting patterns from blocks wherein a rigid rod pivotally attached at one end thereof from a frame is provided with an intermediate discontinuity of a relatively short extent across which a cutting element is maintained in taut condition.

Still another object of the present invention is the provision of apparatus for cutting patterns in blocks wherein a rigid rod constituting the means by which a pattern traced at one point is transmitted to the cutting means at another point, is provided with extensible tracing means so that the effective overall length thereof may be increased to permit effective tracing of the outline of the configuration being traced.

Other objects, features and advantages of the invention shall become apparent as the description thereof proceeds when considered in connection with the accompanying illustrative drawings.

DESCRIPTION OF THE DRAWING

In the drawing which illustrates the best mode presently contemplated for carrying out the present invention:

FIG. 1 is a perspective view of apparatus for cutting patterns constructed in accordance with the instant invention:

FIG. 2 is a side view thereof;

FIG. 3 is a partial perspective view on an enlarged scale showing in particular the operation of the cutting means of the present invention;

FIG. 4 is an enlarged section taken along the line 4—4 of FIG. 2 showing in particular the manner in which the rigid rod means of the present invention is mounted to the frame;

FIG. 5 is an elongated section taken along the line 5—5 of FIG. 2 showing details of the tracing means;

FIG. 6 is a perspective view showing the manner in which the patterned block is utilized as a mold to form a radiotherapy shield;

DESCRIPTION OF THE INVENTION

Figure 7:
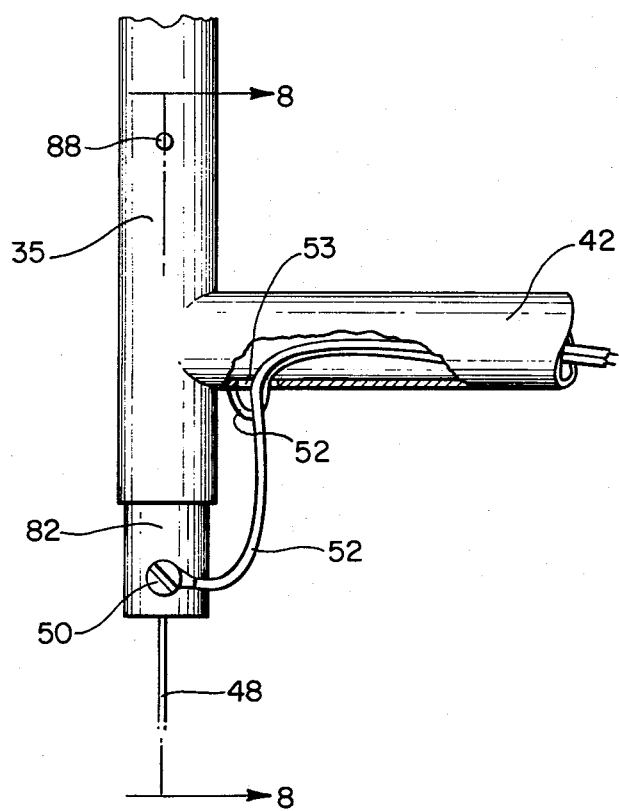
FIG. 7 is a fragmentary elevational view on an enlarged scale, showing the mounting for the cutting wire.

Turning now to the drawings and initially to FIGS. 1 and 2 thereof, the pattern cutting apparatus 10 of the present invention and its overall environment is depicted. Table 12 is shown as having a translucent panel 14 lighted from below by means of a lamp 16. An electrical control panel 18 is suitably attached either to the table 12 or to the frame 20. The frame may be attached directly to the table 12 as depicted or alternatively may be free standing. Control panel 18, as utilized, regulates the amount of electricity passing through the electrically heated cutting wire as will hereinafter be more fully explained and is accordingly connected to a suitable power source (not shown).

A first bracket 22 is mounted at the top of the frame 20 and is adjustable upwardly and downwardly thereon by slide means 24 of known construction. The end of the bracket 22 is provided with a bifurcated portion 26 in which the outer housing 28 of a universal joint is attached by means of screw means 30. The inner or pivotal portions 32 of the universal joint are provided with an interior bore 34 for receipt of the upper section 35 of a rigid rod 36 and maintained in position therein by means of a supporting collar 38 in turn held in position on said rod section 35 by means of a set screw 40. Alternatively, other attachment means which also provide pivotal movement between the rigid rod 36 and the bracket 22 such as ball joints and the like may be utilized.

As best shown in FIG. 3, the rigid rod 36 is provided with an offset portion 42 intermediate the full extent thereof and joining the upper section 35 to the lower section 44. The offset portion 42, which is of a generally C-shaped configuration and preferably of hollow construction, is directly attached to terminal portions of the upper and lower rod sections 35, 44 as by welding or by clamping means (not shown). The discontinuity 46 between the terminal portions of the lower and upper rod sections 44 and 35, respectively, is spanned by means of a wire 48 drawn taut therebetween and spring-loaded, as will hereinafter be described, to which suitable electrical contacts 50 are attached. Suitable electrical conduits 52 serve to transmit electrical current to the spaced contacts 50 and thus through the wire 48 to heat such to the point necessary to accomplish heat cutting of the mold block as will hereinafter be evident. Such conduits may span the discontinuity 46 by attachment to the outside of the C-shaped offset portion 42 by means of tape, clips or the like (not shown) or preferably they may pass through the interior hollow portions thereof via openings 53, provided in the offset portion near the ends thereof, as shown in FIG. 7. This enables the current transmission lines 52 to be directed to the same side of the discontinuity 46 and accordingly reduces the array of wires which must be avoided while mounting and removing mold blocks in the present device.

The lower end of the lower rod section 44 is provided with a tracing means 54 for tracing a pattern such as an X-ray displayed on the face panel 14 from which a blocking shield is desired to be patterned. The tracing means 54 comprises a rigid barrel 56 releasably clamped in the hollow interior of the rod section 44 by means of a screw cap 58. A spring 60 is mounted within the barrel, and a pointer element 62 is positioned below said spring. The pointer extends outwardly from the bottom of the barrel 56 and is provided with a lower tip 64 constructed of or coated with a friction reducing material, such as Teflon. This better enables the pointer 62 to glide across the surface of the X-ray or other pattern 66 to be traced. The barrel 56 on the other hand allows upward or downward adjustability of the tracing means 54 to correspond with the position at which the rigid rod 36 is pivotally attached to bracket 22 at its upper end. It is thus apparent that as the pointer means 54 traces the X-ray or other pattern 66 displayed on the panel 14, corresponding patterns are transmitted along the full extent of the rigid rod 36 by reason of its rigidity and the pivotal movement allowed from its attachment point to the frame 20. Also, since the pointer 62 is continually spring-urged outwardly into contact with the pattern 66 displayed, such pattern may be outlined with a high degree of accuracy.

A second support 68 is positioned by adjustable clamp means 70 along an intermediate portion of the frame 20 proximate the discontinuity 46 and extending within the offset portion 42 of the rigid rod 36. The support 68 is adapted to support a block 72 of a rigid, heat-cuttable material, such as polystyrene foam. After the current is activated by means of control panel 18, the thus heated wire 48 is initially directed to the general area to be traced resulting in a preliminary cut 74. Thereafter the pointer 62 is manually moved around the X-ray pattern 66 to deliniate those body portions which require shielding. Thus, if the heart is to be the organ to be protected or shielded in the radiotherapy treatment of a patient's lung area, then an X-ray of the patient's heart is traced by the pointer 62 so that a similar pattern is transmitted to the block 72 by means of the rigid rod 36 and the taut heated cutting wire 48 to accordingly produce a heart-shaped cut line 76, as depicted in FIG. 3 of the drawing. The cutout 78 corresponding to the shape traced by the cut line 76 is removed from the polystyrene foam block 72, and the cavity 80 formed by such removal is used as a mold for the receipt of shielding material, such as lead or alloys thereof. The resultant composite block is then used as the shielding device in the radiotherapy of a patient.

Thus, it is apparent that the present device enables tracings of X-rays or other patterns to be produced in a smooth and easy manner without the necessity, as in prior art devices, of the operator working against the force of a counterweight which has heretofore been necessary to maintain the cutting wire in a taut condition. The present device reduces or eliminates operator fatigue and thus results in easier and more accurate tracings. This novel device further enables the selection of a greater variety of materials to be used for the cutting wire 48 due to the fact that the wire need not have the strength characteristics of prior art devices since the rigid rod 36 comprised of upper, lower and offset sections 35, 44 and 42, respectively, provide the strength and rigidity needed to accurately transmit the tracing movement to the cutting means. This better assures that the patterns traced are transmitted along a direct straight line path. The relatively short distance across which the wire 48 spans the discontinuity 46 between the upper and lower rod sections 35 and 44 also enables the wire to be more accurately aligned with such sections and form a continuation of the overall straight longitudinal extent of the rod means 36. Also, the relatively short length needed for the cutting wire 48 is desirable from an electrical standpoint and further results in reduced replacement costs.

Figure 8:
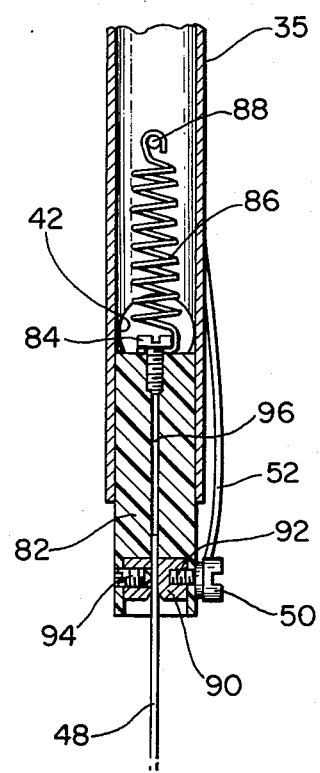
FIG. 8 is a section taken on line 8—8 of FIG. 7.

Since it has been found that the cutting wire 48 sometimes has the tendency to expand under heat, and hence become a little bit slack, which adversely affects the accuracy of the pattern being cut, it has been found desirable to provide a spring-loaded mount for said cutting wire. As will be seen most clearly in FIG. 8, the lower end of rod section 35 telescopingly receives an insulating bushing 82 which is connected at its upper end, as by screw 84, to the lower end of a relatively strong coil spring 86, which in turn is secured at its upper end to rod section 35, as by pin 88. As will be seen, the lower end of bushing 82, which extends downwardly below the end of rod section 35, is provided with an electrically conductive insert 90, secured thereto by screw 92, the head of which functions as contact 50, and by set screw 94. An aligned bore 96 extends through insert 90 and bushing 82 and receives the upper end of wire 48, which is secured in place by set screw 94. Since the lower end of wire 48 is fixedly secured to the upper end of rod section 44, it will be clear that the spring assembly just described will serve to maintain continuous resilient pressure on wire 48 whereby the latter will always be maintained taut, even if there is some degree of expansion of the wire. Obviously, the spring 86 must be of sufficient strength so as not to yield during the cutting operation.

The adjustable mounts 24 and 70 permit the effective length of rod 36 to be increased or decreased as may be necessary or desirable depending on the peripheral size of the pattern to be traced, and permit corresponding adjustment of support 68.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A device for cutting patterns in mold blocks and the like comprising, a frame, a rigid rod attached at one end thereof to said frame for pivotal movement therewith, said rod having tracing means at the other end thereof for tracing a pattern and an offset portion intermediate said ends, said offset portion defining a discontinuity in said rod, means for supporting a block within said offset portion, and cutting means tightly spanning said discontinuity for cutting said block in a pattern corresponding to a pattern traced by said tracing means, said cutting means comprising a spring-loaded, electrically heated wire.

2. The device set forth in claim 1, said tracing means being extensible from said other rod end.

3. The device set forth in claim 2, said extensible tracing means including a spring mounted at said other rod end and a pointer element mounted adjacent said spring, said spring continuously urging said pointer element outwardly of said other rod end.

4. The device set forth in claim 3, said spring and said pointer element being mounted in a housing, said housing slidably clamped to said other rod end.

5. The device set forth in claim 1, said rod having aligned upper and lower portions, said offset portion comprising a hollow rod section of generally C-shaped configuration, such generally C-shaped section connecting said upper and lower rod portions.

6. The device set forth in claim 5, further comprising electrical conduits for feeding electricity to said cutting wire, at least one of said conduits extending along the interior of said hollow C-shaped member.

7. The device set forth in claim 1, said means for supporting said block including a platform connected to said frame and adjustably movable therewith.

8. The device set forth in claim 1, said means for pivotally connecting said rod one end to said frame is adjustably movable, and comprises a universal joint.

9. The device set forth in claim 3, said pointer element having a low friction tracing tip.

10. The device set forth in claim 9, said low friction tip comprising Teflon.

* * * * *

UNITED STATES PATENT OFFICE
CERTIFICATE OF CORRECTION

Patent No. 3,968,711     Dated July 13, 1976

Inventor(s) William Donald Wilson

It is certified that error appears in the above-identified patent and that said Letters Patent are hereby corrected as shown below:

[73] Assignee: Huestic Machine Corporation should be: Huestis Machine Corporation.

Signed and Sealed this

Second Day of November 1976

[SEAL]

Attest:

RUTH C. MASON
Attesting Officer

C. MARSHALL DANN
Commissioner of Patents and Trademarks